United States Patent
Sarkar et al.

(10) Patent No.: US 8,977,350 B2
(45) Date of Patent: Mar. 10, 2015

(54) METHODS FOR ECTOPY REJECTION FOR ATRIAL FIBRILLATION DETECTION BASED ON VENTRICULAR CYCLE LENGTHS

(75) Inventors: Shantanu Sarkar, Roseville, MN (US); Eduardo N. Warman, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 462 days.

(21) Appl. No.: 13/050,091

(22) Filed: Mar. 17, 2011

(65) Prior Publication Data
US 2012/0238891 A1 Sep. 20, 2012

(51) Int. Cl.
A61B 5/04 (2006.01)
A61B 5/02 (2006.01)
A61B 5/0468 (2006.01)
A61N 1/362 (2006.01)
A61N 1/39 (2006.01)
A61B 5/00 (2006.01)

(52) U.S. Cl.
CPC ............ *A61B 5/0468* (2013.01); *A61N 1/3624* (2013.01); *A61N 1/395* (2013.01); *A61B 5/7282* (2013.01)
USPC ............................ 600/518; 600/516; 600/508

(58) Field of Classification Search
CPC .. A61B 5/0468; A61B 5/7282; A61B 5/7264; A61N 1/3624; A61N 1/395; A61N 1/3622
USPC .................................. 600/515–518, 508–510
See application file for complete search history.

(56) References Cited

U.S. PATENT DOCUMENTS

| | | | |
|---|---|---|---|
| 6,718,197 B1 | 4/2004 | Carlson et al. | |
| 7,031,765 B2 | 4/2006 | Ritscher | |
| 7,537,569 B2 | 5/2009 | Sarkar | |
| 7,623,911 B2 | 11/2009 | Sarkar | |
| 7,627,368 B2 | 12/2009 | Houben | |
| 7,853,317 B2 | 12/2010 | Duann | |
| 2002/0065473 A1 | 5/2002 | Wang et al. | |
| 2004/0092836 A1 | 5/2004 | Ritscher et al. | |
| 2008/0161703 A1* | 7/2008 | Houben et al. | 600/509 |
| 2008/0183085 A1* | 7/2008 | van Oort et al. | 600/508 |
| 2009/0275849 A1 | 11/2009 | Stewart | |
| 2010/0056940 A1 | 3/2010 | Moorman | |
| 2010/0099995 A1 | 4/2010 | Lian | |
| 2010/0106033 A1 | 4/2010 | Lian | |

OTHER PUBLICATIONS (PCT/US2012/022337) PCT Notification of Transmittal of the International Search Report and the Written Opinion of the International Searching Authority, Apr. 25, 2012.

* cited by examiner

*Primary Examiner* — Catherine Voorhees
(74) *Attorney, Agent, or Firm* — Michael C. Soldner

(57) ABSTRACT

A medical device performs a method to classify a cardiac rhythm. Differences between cycle lengths in a first heart chamber are determined during an established time interval. Evidence of ectopy associated with irregular coupling intervals is detected from the signal during the established time interval. A rhythm classification output corresponding to a second heart chamber at the expiration of the established time interval is provided in response to the consecutive cycle length differences and the evidence of ectopy associated with irregular coupling intervals.

24 Claims, 12 Drawing Sheets

METHODS FOR ECTOPY REJECTION FOR ATRIAL FIBRILLATION DETECTION BASED ON VENTRICULAR CYCLE LENGTHS

TECHNICAL FIELD

The disclosure relates generally to implantable medical devices and, in particular, to methods for detecting atrial arrhythmias using ventricular cycle lengths.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

In the past, atrial arrhythmias have been largely undertreated due to the perception that these arrhythmias are relatively benign. As more serious consequences of persistent atrial arrhythmias have come to be understood, such as an associated risk of relatively more serious ventricular arrhythmias and stroke, there is a growing interest in monitoring and treating atrial arrhythmias.

Methods for discriminating arrhythmias that are atrial in origin from arrhythmias originating in the ventricles have been developed for use in dual chamber implantable devices wherein both an atrial EGM signal and a ventricular EGM signal are available. Discrimination of arrhythmias can rely on event intervals (PP intervals and RR intervals), event patterns, and EGM morphology. Such methods have been shown to reliably discriminate ventricular arrhythmias from supraventricular arrhythmias. However, in single chamber implantable devices, subcutaneous implantable devices, and external monitoring devices, an adequate atrial EGM signal having acceptable signal-to-noise ratio is not always available for use in detecting and discriminating atrial arrhythmias.

DETAILED DESCRIPTION

In the following description, references are made to illustrative embodiments for carrying out the methods described herein. It is understood that other embodiments may be utilized without departing from the scope of the disclosure.

In various embodiments, ventricular signals are used for determining successive ventricular cycle lengths for use in detecting atrial arrhythmias. The atrial arrhythmia detection methods do not require an atrial signal source. The methods presented herein may be embodied in software, hardware or firmware in implantable or external medical devices. Such devices include implantable monitoring devices having cardiac EGM/ECG monitoring capabilities and associated EGM/ECG sense electrodes, which may be intracardiac, epicardial, or subcutaneous electrodes.

The methods described herein can also be incorporated in implantable medical devices having therapy delivery capabilities, such as single chamber or bi-ventricular pacing systems or ICDs that sense the R-waves in the ventricles and deliver an electrical stimulation therapy to the ventricles. The atrial arrhythmia detection methods presently disclosed may also be incorporated in external monitors having ECG electrodes coupled to the patient's skin to detect R-waves, e.g. Holter monitors, or within computerized systems that analyze pre-recorded ECG or EGM data. Embodiments may further be implemented in a patient monitoring system, such as a centralized computer system which processes data sent to it by implantable or wearable monitoring devices.

It is also recognized that various embodiments may be implemented in internal or external monitoring systems that include sensors of ventricular activity other than electrical signals from which ventricular cycle length (VCL) measurements can be made. Practice of the methods presented herein is therefore not limited to the use of EGM or ECG signals for measuring VCLs. Other signals, such as pressure signals, blood oximetry signals, flow signals, ventricular wall motion signals, volume-related impedance signals, or other physiological signals responsive to the ventricular cycle, can be used for measuring VCLs. Generally, VCL measurements should have a resolution on the order of about 1 to 20 ms to allow for atrial arrhythmia detection based on VCL irregularity metrics, however, aspects of the presently disclosed methods may be implemented in systems having lower resolution of VCL measurements.

Figure 1:
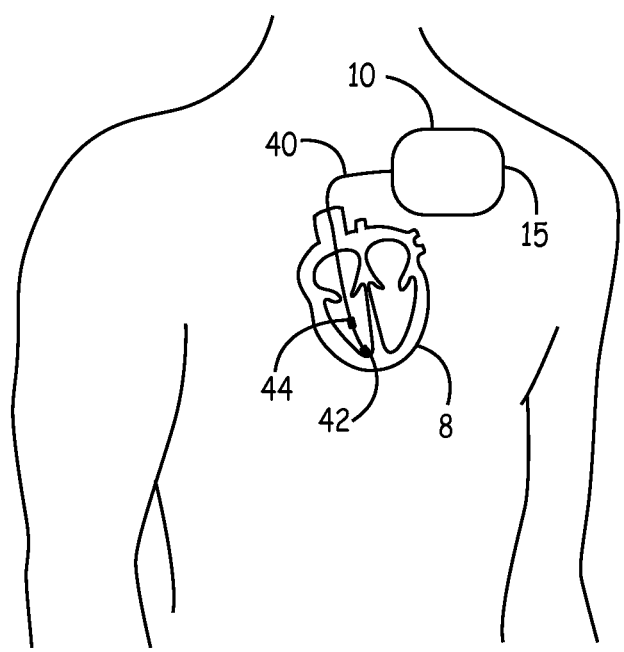
FIG. 1 is an illustration of an implantable medical device (IMD) implanted in a patient and coupled to the patient's heart via a ventricular lead.

FIG. 1 is an illustration of an implantable medical device (IMD) 10 implanted in a patient and coupled to the patient's heart 8 via a ventricular lead. The simplified illustration of IMD 10 may represent a variety of IMDs such as a cardiac pacemaker, implantable cardioverter defibrillator, hemodynamic monitor, ECG recorder, or a drug delivery device. IMD 10 may be coupled to one or more fluid delivery catheters or electrical leads 40. In the embodiment shown, lead 40 is used for carrying one or more electrodes and/or other physiological sensors used for monitoring one or more physiological signals and delivering electrical stimulation therapies to the patient's heart 8. IMD 10 may alternatively be embodied as a leadless device wherein sensors and/or electrodes are incorporated in or on the housing 15 of IMD 10.

Lead 40 is a right ventricular lead including one or more electrodes 42 and/or sensors 44. Electrode 42 may be used in conjunction with IMD housing 15 for sensing ventricular EGM signals. Lead 40 may be provided with a second electrode for bipolar sensing of EGM signals. In one embodiment, sensor 44 is used for sensing a ventricular pressure signal, or other signal correlated to the cyclical ventricular activity, which may be used in some embodiments for determining VCLs.

Figure 2:
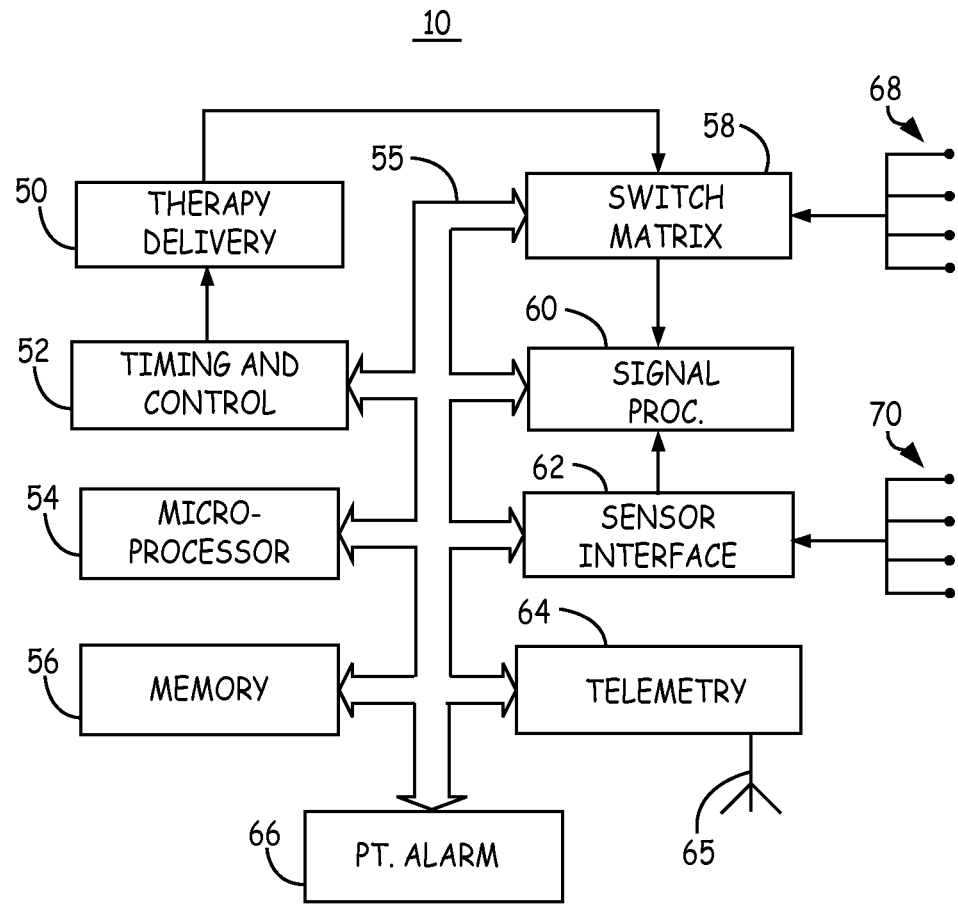
FIG. 2 is a functional block diagram of the IMD of FIG. 1.

FIG. 2 is a functional block diagram of IMD 10. IMD 10 generally includes timing and control circuitry 52 and an operating system that may employ microprocessor 54 or a digital state machine for timing sensing and therapy delivery functions and controlling other device functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may be lead-based electrodes, leadless electrodes incorporated on IMD 10, and/or the IMD housing configured for use as a can or case electrode. Electrodes 68 are used for sensing electrical ventricular signals and may be used for sensing other signals within the body, such as impedance signals. Cardiac electrical signals are sensed using any of electrodes 68 for detecting and diagnosing heart rhythms and may be used for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias.

IMD 10 may include other physiological sensors 70. Physiological sensors 70 may include pressure sensors, accelerometers, flow sensors, blood chemistry sensors, activity sensors or other implantable physiological sensors. Sensors 70 are coupled to IMD 10 via a sensor interface 62 which provides sensor signals to signal processing circuitry 60. Sensor interface 62 may include integrated circuitry for providing sensor drive signals or excitation signals to sensors 70 and for receiving a raw signal and converting to an analog or digital sensor signal for sensing physiological events. Sensor signals are used by microprocessor 54 for detecting physiological events or conditions. For example, IMD 10 may monitor heart wall motion, blood pressure, blood chemistry, respiration, or patient activity. Monitored signals may be used for diagnosing a patient condition or for sensing the need for delivering or adjusting a therapy under control of the operating system.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. Memory 56 is used to store operating commands and data for controlling device operation and for later retrieval to diagnose device function or patient condition. In accordance with the various embodiments, parameter values and thresholds used for detecting atrial arrhythmias from a ventricular signal are stored in memory 56. A portion of memory 56 is allocated for storing ventricular cycle length data over predetermined intervals of time and used for determining a metric of VCL irregularity as will be described herein.

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit. Data from IMD 10 may be transmitted to a centralized patient database to enable a physician to monitor the patient from a remote location.

IMD 10 may include patient alarm circuitry 66 for generating audible tones, a perceptible vibration, muscle stimulation or other sensory stimulation for notifying the patient that an alarm condition has been detected by IMD 10.

Figure 3:
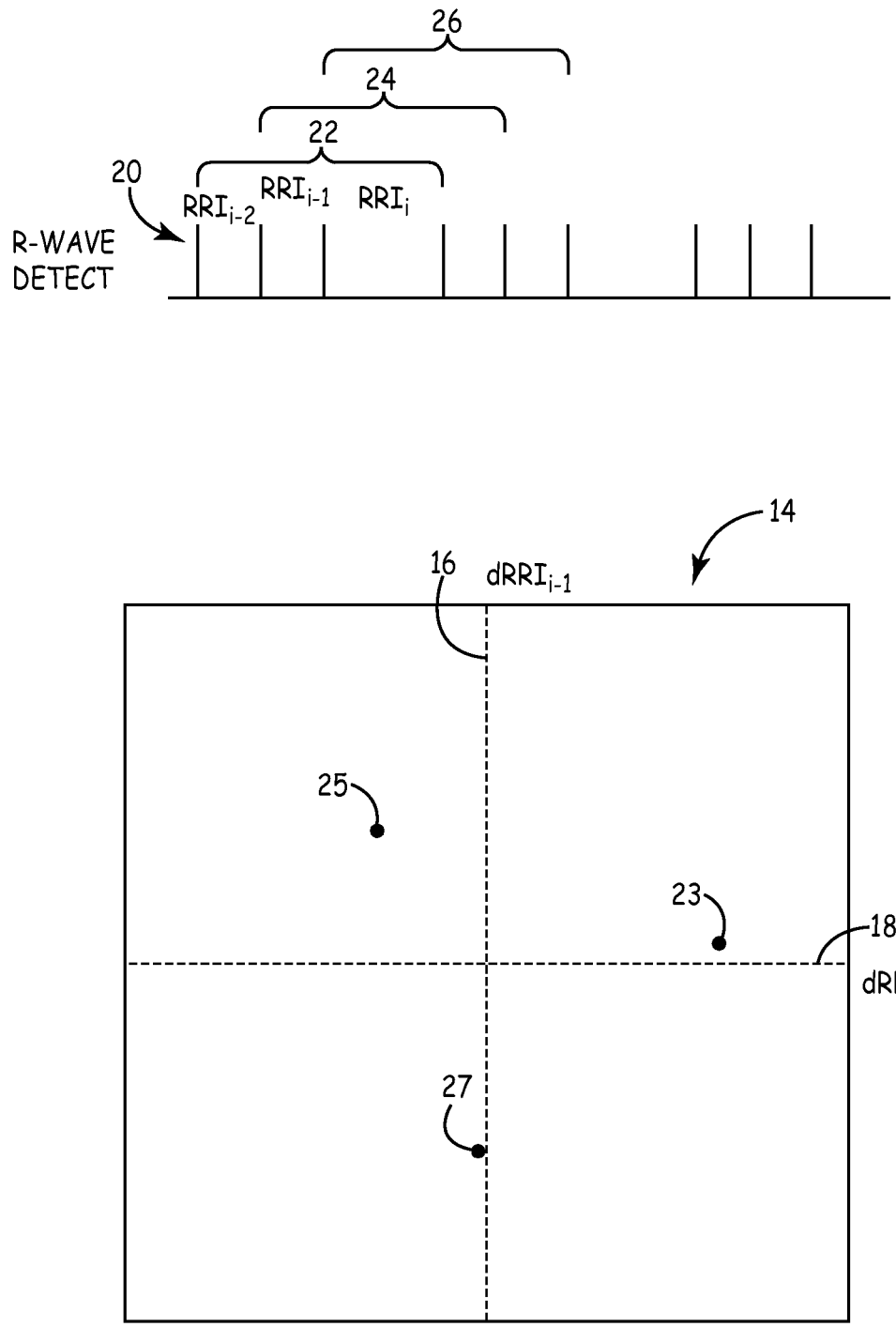
FIG. 3 illustrates the generation of a Lorenz scatter plot of ventricular cycle length data for use in detecting atrial arrhythmias.

FIG. 3 illustrates the generation of a Lorenz scatter plot of VCL data for use in detecting atrial arrhythmias. The differences between consecutive RR intervals ($\delta$RRs) are plotted for a time series of R-R intervals (RRIs). The Lorenz plot 14 is a Cartesian coordinate system defined by $\delta RR_i$ along the x-axis 18 and $\delta RR_{i-1}$ along the y-axis 16. As such, each plotted point in a Lorenz plot is defined by an x-coordinate equaling $\delta RR_i$ and a y-coordinate equaling $\delta RR_{i-1}$. $\delta RR_i$ is the difference between the $i^{th}$ RRI and the previous RRI, $RR_{i-1}$. $\delta RRI_{i-1}$ is the difference between $RRI_{i-1}$ and the previous RRI, $RRI_{i-2}$. As such, each data point plotted on the Lorenz plot 14 represents a VCL pattern relating to three consecutive VCLs: $RRI_i$, $RRI_{i-1}$ and $RRI_{i-2}$, measured between four consecutively sensed R-waves. As noted previously, VCL information is not limited to detection of R-waves and determination of RRIs. The terms RRI and $\delta RR_i$ as used herein refer generally to a measurement of VCL and the difference between two consecutive VCL measurements, respectively, whether the VCL measurements were derived from a series of R-wave detections from an EGM or ECG signal or another ventricular cycle event detection from any other physiological signal (e.g. a peak pressure determined from a pressure signal). For the sake of illustration, the embodiments described herein often refer to R-wave detections for performing VCL measurements and the determination of ($\delta RR_i$, $\delta RR_{i-1}$) points.

In FIG. 3, a series of R-wave events 20 are shown. In order to plot a point on the Lorenz plot area 14, a ($\delta RR_i$, $\delta RR_{i-1}$) point is determined by measuring successive RRIs determined from the R-wave events 20. In the example shown, a first series 22 of three consecutive RRIs and $RRI_i$) provides the first data point 23 on the Lorenz plot area 14. $\delta RR_{i-1}$, which is the difference between $RRI_{i-2}$ and $RRI_{i-1}$ is approximately 0. $\delta RR_i$, the difference between the $RRI_{i-1}$ and $RRI_i$, is a positive change. Accordingly, a ($\delta RR_i$, $\delta RR_{i-1}$) point 23 having a y-coordinate near 0 and a positive x-coordinate is plotted in the Lorenz plot 14, representing the first series 22.

The next series 24 of three RRIs provides the next ($\delta RR_i$, $\delta RR_{i-1}$) point 25 having a negative x-coordinate ($RRI_{i-1}$ being less than $RRI_{i-2}$) and a positive y-coordinate ($RRI_{i-1}$ being greater than $RRI_{i-2}$). This process of plotting ($\delta RR_i$, $\delta RR_{i-1}$) points continues with the three cycle series 26 providing data point 27 and so on.

Methods have been developed for detecting atrial arrhythmias based on the irregularity of ventricular cycles measured by RR intervals that exhibit discriminatory signatures when plotted in a Lorenz scatter plot such as the plot shown in FIG. 3. One such method is generally disclosed by Ritscher et al. in U.S. Pat. No. 7,031,765, incorporated herein by reference in its entirety. Other methods are generally disclosed by Sarkar, et al. in U.S. Pat. No. 7,623,911 and in U.S. Pat. No. 7,537,569 and by Houben in U.S. Pat. No. 7,627,368, all of which patents are also incorporated herein by reference in their entirety.

Figure 4:
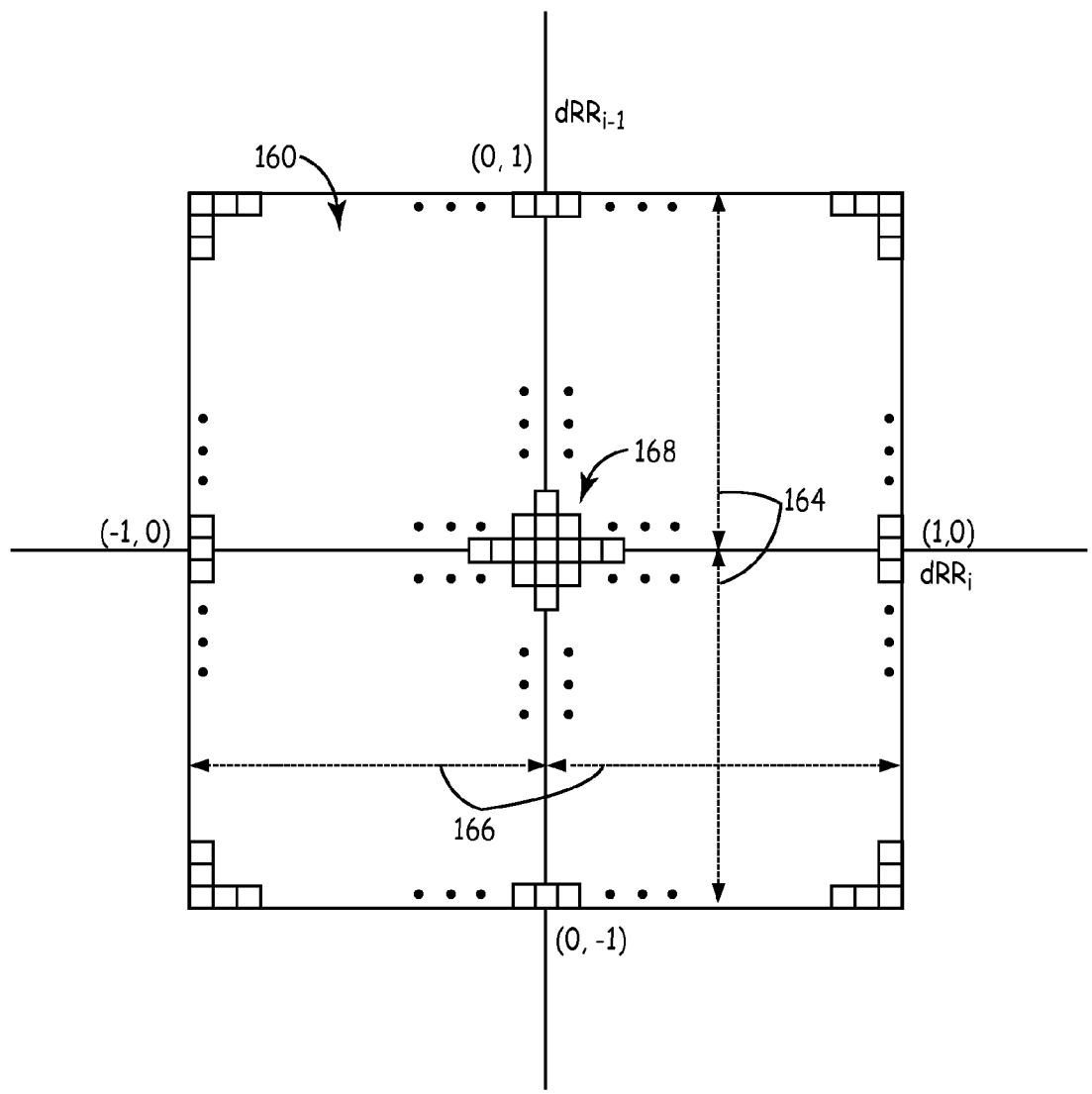
FIG. 4 is a diagram of a two-dimensional histogram representing the Lorenz plot area.

FIG. 4 is a diagram of a two-dimensional histogram representing the Lorenz plot area. Generally, the Lorenz plot area 14 shown in FIG. 3 is numerically represented by a two-dimensional histogram 160 having predefined ranges 166 and 164 in both positive and negative directions for the $\delta RR_i$ and $\delta RR_{i-1}$ coordinates, respectively. The two-dimensional histogram is divided into bins 168 each having a predefined range of $\delta RR_i$ and $\delta RR_{i-1}$ values. In one example, the histogram range might extend from −1200 ms to +1200 ms for both $\delta RR_i$ and $\delta RR_{i-1}$ values, and the histogram range is divided into bins extending 7.5 ms in each of the two dimensions resulting in a 160 bin×160 bin histogram. The successive RRI differences determined over a detection time interval are used to populate the histogram 160. Each bin stores a count of the number of ($\delta RR_i$, $\delta RR_{i-1}$) data points falling into the given bin range. The bin counts are then be used in determining RRI variability metrics and populated bin patterns for determining a cardiac rhythm type.

One challenge in applying an AF discrimination algorithm is the discrimination of AF from a rhythm that includes prolonged runs of frequent ectopy (premature contractions). During a run of frequent ectopic events, highly variable RRIs may occur. For example, premature atrial contractions (PACs) conducted to the ventricles may depolarize the ventricles at irregular coupling intervals related to underlying variability of a sinus rhythm. Patterns of ($\delta RR_i$, $\delta RR_{i-1}$) data points populating a Lorenz plot area histogram 160 may result in an AF evidence score computed based on histogram bin counts that meets an AF detection threshold, causing a false AF detection during a run of frequent PACs.

Figure 5:
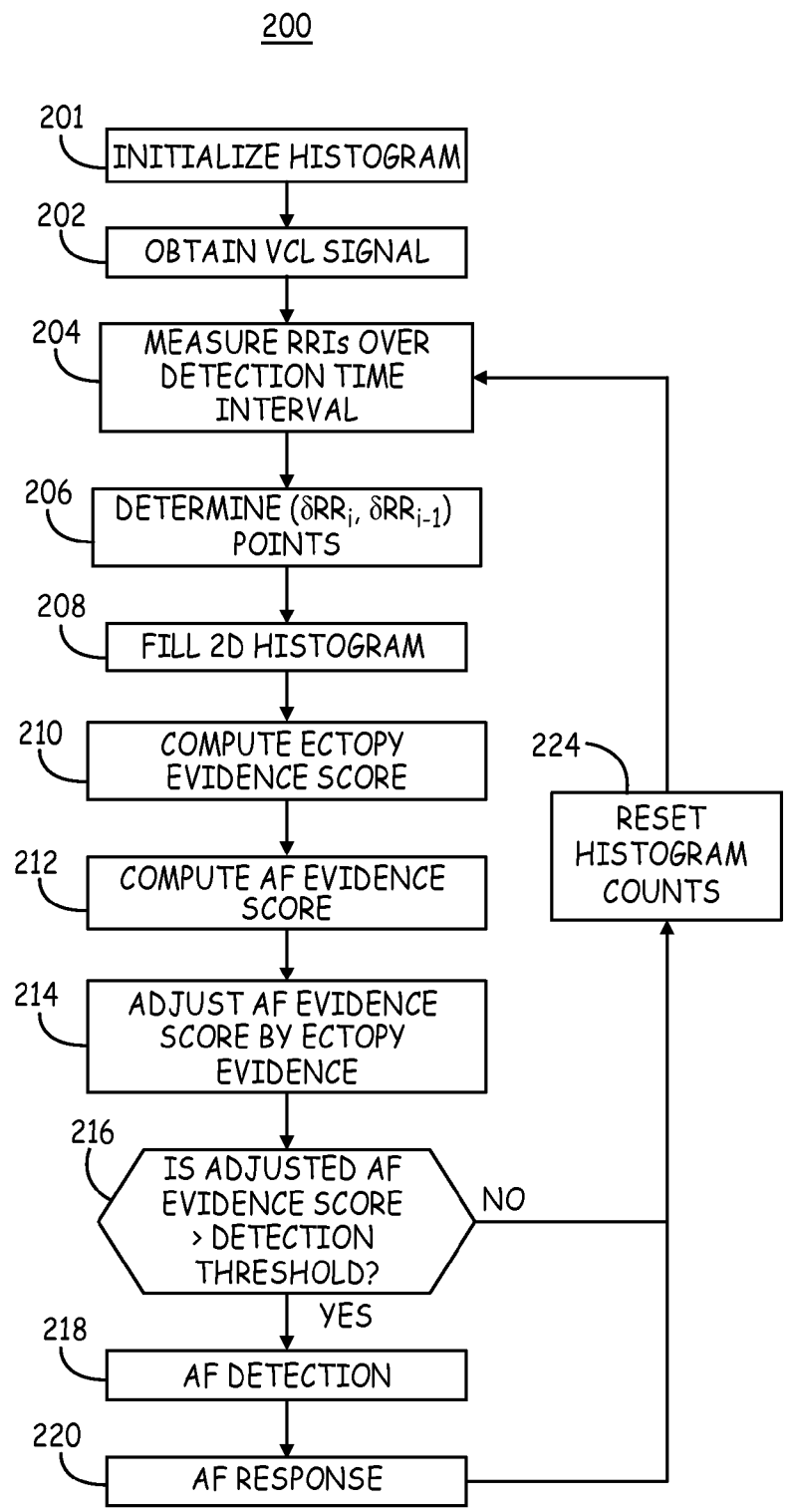
FIG. 5 is a flow chart of one method for using evidence of ectopy during a cardiac rhythm detection algorithm according to one embodiment.

FIG. 5 is a flow chart 200 of a method for using evidence of ectopy during a cardiac rhythm detection algorithm according to one embodiment. Flow chart 200 and other flow charts presented herein are intended to illustrate the functional operation of the device, and should not be construed as reflective of a specific form of software or hardware necessary to practice the methods described herein. It is believed that the particular form of software, firmware and/or hardware will be determined primarily by the particular system architecture employed in the device and by the particular detection and therapy delivery methodologies employed by the device. Providing software, firmware and hardware to accomplish the methods described herein in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Flow chart 200 is directed to atrial fibrillation (AF) detection, however it is recognized that aspects of the methods described may be applied to the detection of other atrial arrhythmias, such as atrial flutter. At block 201, a histogram is initialized by defining the number of histogram bins for each coordinate axis and corresponding bin ranges of a two-dimensional Lorenz plot area. A counter for each histogram bin is set to zero.

At block 202, a physiological signal containing VCL information is obtained. The signal may be a ventricular EGM signal or an ECG signal but is not limited to being a cardiac electrical signal. For illustrative purposes, the methods described herein relate primarily to the use of a cardiac EGM or ECG signal from which R-waves are sensed for measuring VCLs as RRIs.

At block 204 RRI measurements are collected over a predetermined rhythm detection time interval, for example for approximately 2 minutes. Data collected from the ventricular signal information over the established detection time interval is used to classify the atrial rhythm at the end of the detection time interval. At block 206, ($\delta RR_i$, $\delta RR_{i-1}$) data points are determined from the measured RRIs.

The ($\delta RR_i$, $\delta RR_{i-1}$) data points are used to populate the 2D histogram at block 208. As described previously, a 2D scatter plot is generated wherein each point is defined by an x-coordinate corresponding to the difference between an RRI and the previous RRI and the y-coordinate corresponding to the difference between the previous RRI and the next previous RRI. The histogram is filled by incrementing a counter for the histogram bin which corresponds to the coordinate values of each ($\delta RR_i$, $\delta RR_{i-1}$) data point. The methods described herein are generally implemented using a 2D histogram, however aspects of the methods may alternatively be implemented using 1D or higher dimensional scatter plots of VCL data.

At block 210, an analysis of the VCL signal is performed for determining evidence of ectopy that may produce irregular coupling intervals. The ectopy evidence is used in providing a rhythm classification output at the expiration of the detection time interval. The analysis at block 210 may include an analysis of the morphology of the signal itself (an EGM or ECG signal in this example), an analysis of RRI measurements determined from the signal, an analysis of a cluster signature of the ($\delta RR_i$, $\delta RR_{i-1}$) data points in the Lorenz plot histogram, or any combination thereof. Methods for computing an ectopy evidence score for determining evidence of ectopy will be described in greater detail below.

Figure 8:
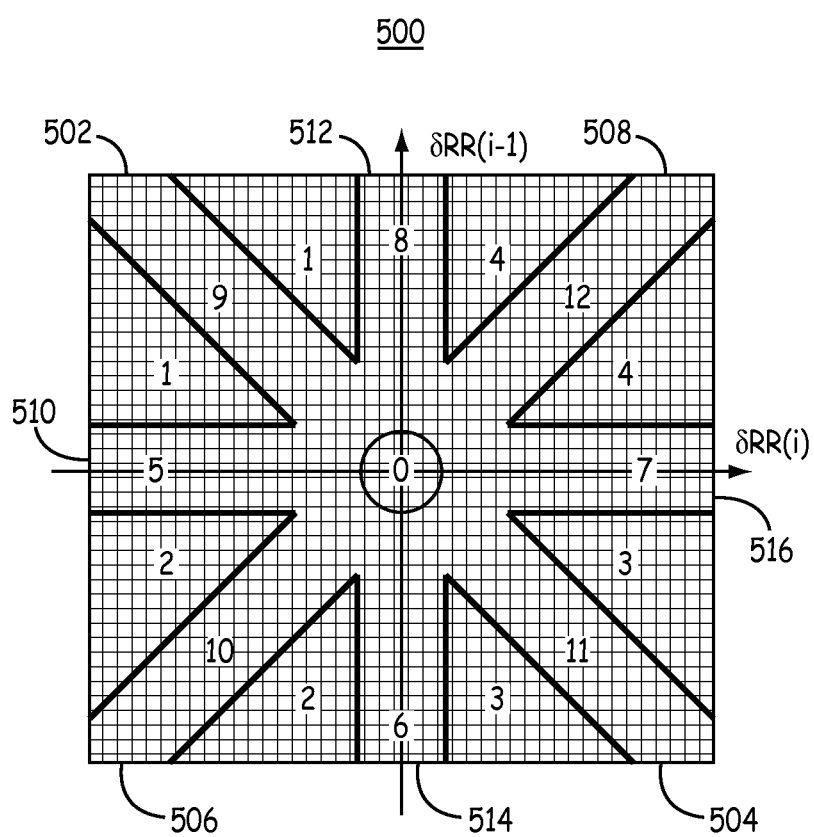
FIG. 8 is a Lorenz plot area shown divided into two-dimensional histogram bins.

At block 212, an RRI variability metric (or more generally a VCL variability metric) is determined from the populated histograms. Generally, the more histogram bins that are occupied, i.e. the more sparse the distribution of ($\delta RR_i$, $\delta RR_{i-1}$) points, the more irregular the VCL during the detection time interval. As such, a metric of the RRI variability can be used for detecting atrial fibrillation, which is associated with highly irregular VCL. In one embodiment, an RRI variability metric for detecting AF, referred to as an AF score is computed as generally described in the above-incorporated '911 patent. Briefly, the AF score may be defined by the equation:

AF Evidence=Irregularity Evidence−Origin Count−PAC Evidence wherein Irregularity Evidence is the number of occupied histogram bins outside a Zero Segment defined around the origin of the Lorenz plot area (see segment labeled "0" in FIG. 8). During normal sinus rhythm or highly organized atrial tachycardia, nearly all points will fall into the Zero Segment surrounding the plot origin because of the relatively small, consistent differences between regular RRIs. A high number of occupied histogram bins outside the Zero Segment, determined as the metric Irregularity Evidence, is therefore positive evidence for AF.

The Origin Count is the number of points in the "Zero Segment" defined around the Lorenz plot origin. A high Origin Count indicates regular RRIs, a negative indicator of AF, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with PACs that occur at regular coupling intervals and present regular patterns of RRIs. These specific forms of regular PACs are associated with bigeminy (short-short-long RRIs) or trigeminy (short-short-short-long RRIs).

In other embodiments, an AF score or other RRI variability score for classifying an atrial rhythm may be computed as described in any of the above-incorporated '765, '911, '569 and '368 patents.

At block 214, the AF evidence score is adjusted by the ectopy evidence score. A high degree of evidence for the presence of ectopy will reduce the AF score. Generally, the ectopy evidence will either reduce the AF evidence score or cause no change to the AF evidence score though in some embodiments an ectopy evidence metric may increase the AF evidence score when no evidence for ectopy is found.

The adjusted AF score will be compared to a threshold for detecting AF at block 216. If the score crosses a detection threshold, AF detection is made at block 218. A response to AF detection is made at block 220, which may include withholding a ventricular therapy, applying atrial therapy, storing data, or triggering other signal acquisition or analysis. The AF response may be to generate a patient alarm or deliver or adjust a therapy.

The RRI measurements continue to be performed after an AF detection to fill the histogram during the next detection time interval by returning to block 204. After each detection time interval, the histogram bins are re-initialized to zero at block 224 for the next detection time interval. A new RRI variability metric and new ectopy evidence score determined at the end of each detection time interval may be used to determine if a detected AF episode is sustained or terminated.

Figure 6:
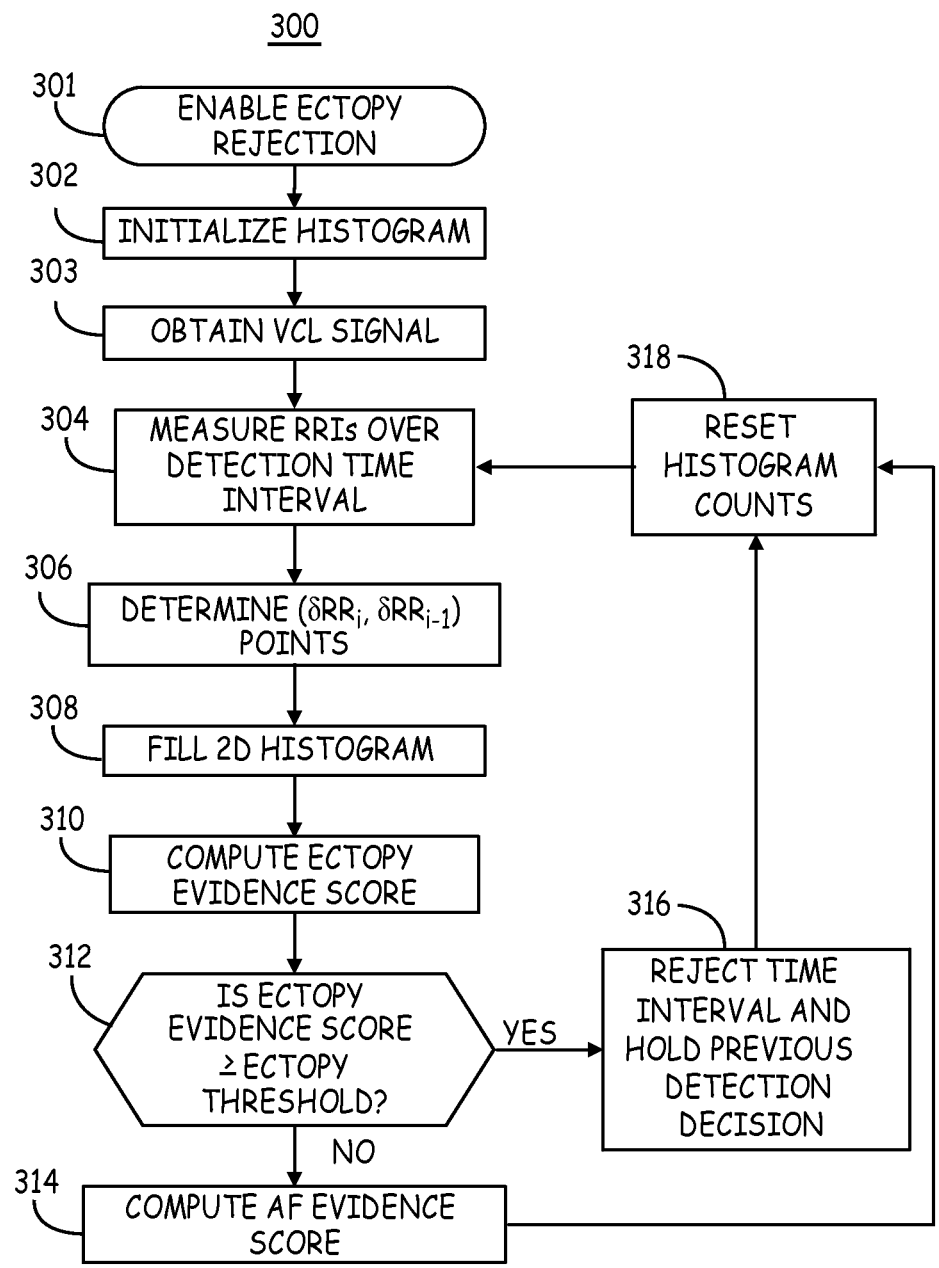
FIG. 6 is a flow chart of an alternative method for using evidence of ectopy during a cardiac rhythm detection algorithm.

FIG. 6 is a flow chart 300 of an alternative method for using evidence of ectopy during a cardiac rhythm detection algorithm. At block 301, a clinician may programmably select to enable ectopy rejection. The method shown in flow chart 300, as well as the method generally shown in FIG. 5, may be enabled by a clinician in patients who are observed to experience frequent ectopy or in whom false detection of AF due to runs of ectopy has occurred.

At blocks 302 through 308, a Lorenz plot area histogram is initialized; a ventricular signal is obtained for measuring RRIs over a detection time interval and to generate ($\delta RR_i$, $\delta RR_{i-1}$) data points for filling the 2D histogram as described previously. An ectopy evidence score is computed at block 310 using the VCL signal directly and/or the histogram data. If the ectopy evidence score is equal to or greater than an ectopy detection threshold, as determined at block 312, the detection time interval is not used to make a rhythm classification decision. A rhythm determination made at the end of the preceding detection time interval is maintained at block 316, and the current detection time interval is effectively rejected due to evidence of a run of ectopy.

If the ectopy evidence score does not reach an ectopy detection threshold at block 312, an AF evidence score (or other RRI variability metric) is computed at block 314. The AF evidence score (or other RRI variability metric) is used for classifying the atrial rhythm at the end of the detection time interval, e.g. as generally described above in conjunction with FIG. 5.

After either rejecting the time interval or computing an AF evidence score, the process resets the histogram counts to zero at block 318 and begins collecting RRI measurements over the next detection time interval.

To summarize, an ectopy evidence score may be used to either adjust an AF evidence score or other metric of RRI variability used to detect and classify a cardiac rhythm (as shown in FIG. 5) or to reject an associated detection time interval (as shown in FIG. 6) to avoid falsely detecting a run of ectopy as AF. A combination of these uses of an ectopy evidence score may also be employed. For example if the ectopy evidence score reaches a first threshold, it may be used to adjust the AF evidence score or other metric used to classify the cardiac rhythm. If the ectopy evidence score reaches a second threshold associated with stronger or more frequent evidence of ectopy, the detection algorithm may reject the current time interval and maintain a previous rhythm classification.

Further, in other embodiments multiple methods may be employed to compute ectopy evidence. Ectopy evidence computed by a less computationally intensive approach and reaching a detection threshold may trigger the computation of ectopy evidence by a more accurate but more computationally intensive approach.

In still other embodiments, if an AF detection has been made upon expiration of a preceding detection time interval, the AF detection may be changed in response to an ectopy evidence score meeting an ectopy detection threshold. The rhythm classification may be changed to a sinus rhythm with ectopy or may be held indeterminate until the next detection interval. In any of these embodiments, an ectopy evidence score is determined and used to provide a rhythm classification output at the expiration of the detection time interval; the output may be a value for adjusting a RRI variability score or a rejection of the current time interval.

Figure 7:
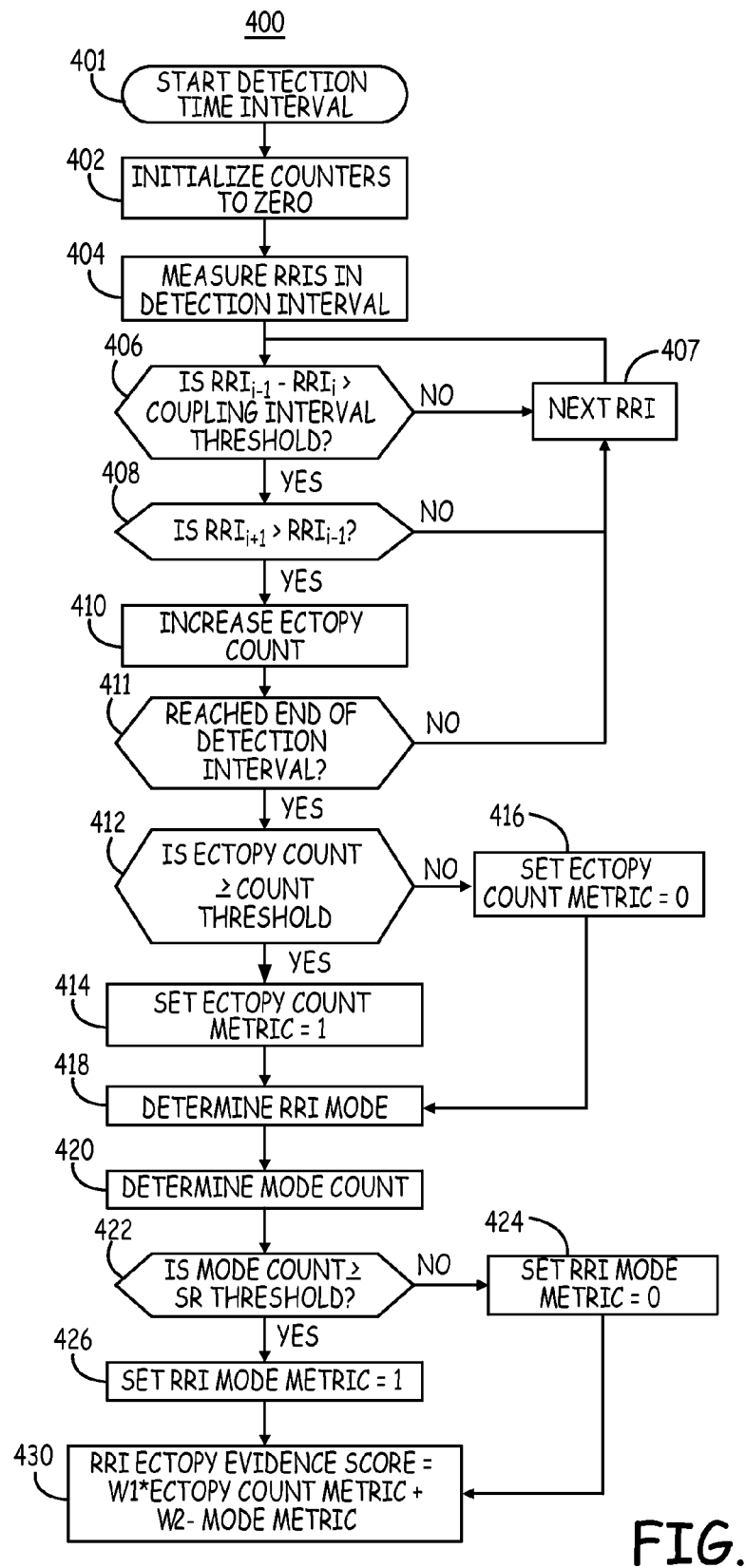
FIG. 7 is a flow chart of one method for determining an ectopy metric for use in a cardiac rhythm determination algorithm.

FIG. 7 is a flow chart 400 of one method for determining an ectopy metric for use in a cardiac rhythm determination algorithm. As used herein, an ectopy metric generally refers to a measure of one or more signal features that provide either positive or negative evidence of ectopy. One or more ectopy metrics may be used to compute the ectopy score referred to in flow charts 200 and 300 of FIGS. 5 and 6, respectively, which is used to provide a rhythm classification output at the end of each detection time interval.

Ectopic beats occurring at irregular coupling intervals may be originating in the atria, the ventricles or a combination of both. When originating in the atria as PACs, the PACs can be conducted to the ventricles at irregular coupling intervals, e.g. due to variability in an underlying sinus rhythm. The method shown by flow chart 400 and other methods described herein are directed to detecting ectopy (atrial, ventricular or both) occurring at irregular coupling intervals that confounds the detection of AF.

The method shown in flow chart 400 is performed for each detection time interval to provide an ectopy evidence metric at the expiration of the detection time interval. Upon starting a detection time interval (block 401), an ectopy counter and a mode counter are initialized to zero at block 402.

RRIs during the detection time interval are measured at block 404. Each sequence of three consecutive RRIs $RRI_{i-1}$, $RRI_i$ and $RRI_{i+1}$) is examined at blocks 406 and 408 to determine if the intervals are likely to be associated with an ectopic event. The ectopic event could be a premature ventricular contraction (PVC) or a conducted PAC. At block 406, a difference between a preceding RRI ($RRI_{i-1}$) and a current RRI ($RRI_i$) is compared to a coupling interval threshold. The coupling interval threshold is a pre-defined value (or could be a percentage of a previously measured RRI) corresponding to a coupling interval of a premature event. If the difference is less than or equal to the coupling interval threshold, the current sequence of three RRIs is not associated with an ectopic event. The process analyzes the next sequence of three RRIs in the detection time interval by advancing to the next RRI at block 407.

If the difference computed at block 406 is greater than the coupling interval, the three beat sequence may be associated with an ectopic event. The comparison at block 406 effectively determines whether an immediately preceding RRI ($RRI_{i-1}$) is longer than the current $RRI_i$ by at least the pre-defined coupling interval threshold. A long interval followed by a short interval will result in a positive difference computed at block 406, and the larger the difference the stronger the evidence of ectopy.

Alternative methods for detecting an RRI that may correspond to an ectopic beat may be used. For example, an ith RRI may be compared directly to a coupling interval threshold at block 406. An RRI equal to or less than a coupling interval threshold may be an ectopic beat interval. If an RRI is equal to or less than a coupling interval, the process may proceed to block 408. Alternatively, a requirement that the ith RRI is less than a defined percentage of the preceding may be applied at block 406. In general, an analysis of the measured RRIs is performed to identify RRIs that are short compared to an immediately preceding interval and therefore possibly associated with an ectopic event.

At block 408, the last RRI in the three beat sequence, $RRI_{i+1}$ is compared to the first RRI in the three beat sequence, $RRI_{i-1}$. If the last RRI is longer than the first RRI in the three beat sequence, the last RRI likely corresponds to a long pause that typically follows a short RRI associated with an ectopic event. This combination of a short coupling interval immediately followed by a long interval, as identified at decision blocks 406 and 408 is evidence of an ectopic beat. An ectopy counter is increased by one at block 410.

The process continues to analyze three-beat sequences during the detection time interval by advancing to the next RRI at block 407. This process continues until the end of the detection interval has been reached as determined at decision block 411.

If the criteria applied at decision blocks 406 and 408 are not met, the current three beat sequence is unlikely to be associated with an ectopic event. The process advances to the next RRI at block 407 to analyze the next three beat sequence. It is recognized that other criteria may be defined to detect a sequence of RRIs that includes a short interval immediately followed by a long interval that is likely to be an ectopic coupling interval followed by a compensatory pause.

The ectopy count reached at the end of the detection time interval is compared to a count threshold at decision block 412. If the ectopy count is less than a count threshold, an ectopy count metric is set to zero at block 416. If the ectopy count is equal to or greater than an ectopy count threshold, an ectopy count metric is set equal to one at block 414. In this way, the ectopy count is used to either positively (ectopy count metric=1) or negatively (ectopy count metric=0) identify a likely run of frequent ectopic events during the detection time interval. Alternatively, the value of the ectopy count reached at block 410 at the end of a detection time interval may be set as the value of an ectopy count metric at block 414.

At block 418, a statistical mode of the RRIs during the detection time interval is determined. All RRIs measured during the detection time interval may be stored, e.g. in an RRI histogram. The RRI occurring with the highest frequency is determined at block 418. This highest frequency, which may be a maximum histogram bin count in a histogram storing all RRIs, is determined as a mode count at block 420, i.e. the number of measured RRIs occurring at the statistical mode.

The mode count is compared to a sinus rhythm threshold at decision block 422. A high occurrence of RRIs at a regular rate is evidence of sinus rhythm (SR). As such, a high mode count is positive evidence for SR, possibly accompanied with frequent ectopy. If the mode count does not reach a SR threshold, the RRI mode metric is set to zero at block 424 because a low mode count is not evidence of an underlying sinus rhythm. The sinus rhythm threshold may be set as a fraction of the total number of intervals in the detection period. If the mode count does equal or exceed the SR threshold, the high mode count is evidence of an underlying sinus rhythm and the RRI mode metric is set equal to one at block 426. Alternatively, the RRI mode metric may be set equal to the mode count.

An RRI ectopy evidence score is computed at block 430 using a combination of the ectopy count metric and the RRI mode metric. This ectopy evidence score is a combination of metrics based on an analysis of RRIs. A high ectopy count (ectopy count metric) and evidence of an underlying sinus rhythm (high mode metric) indicates a high probability that the heart rhythm is a sinus rhythm with frequent ectopic beats and a reduced likelihood of the rhythm being AF. As such, the RRI ectopy evidence score may be used to either adjust an AF evidence score or reject the current time interval for rhythm classification as described previously. The RRI ectopy score may be a weighted combination of the ectopy count metric and the RRI mode metric. Alternatively, an RRI ectopy score may be a combination of the actual ectopy count determined at block 410 and the actual mode count determined at block 420, which may also be a weighted combination.

The ectopy count and the RRI mode count are two examples of metrics based on measured RRIs that can be used to detect ectopy. Other embodiments may analyze RRI measurements using other criteria for detecting ectopy.

In addition or alternatively to detecting ectopy evidence based on an analysis of RRIs, an analysis of the Lorenz plot histogram bin counts may be used to identify evidence of ectopy. FIG. 8 is a Lorenz plot area 500 shown divided into two-dimensional histogram bins. Varying degrees of organization during atrial tachycardia will result in clusters of points in the Lorenz plot area 500. In order to determine metrics of point cluster signatures, the Lorenz plot area is divided into a number of segments, labeled 0 through 12 in FIG. 8. The segments are defined based on signature patterns of ($\delta RR_i$, $\delta RR_{i-1}$) data points in the Lorenz plot area that occur during different atrial rhythms.

Each point plotted in the two-dimensional Lorenz plot encodes a three cycle pattern and the polarity of the changes in cycle length within the three cycle pattern. Patterns or signatures of point clusters can be used for detecting and classifying atrial rhythms as generally described in the above-incorporated '911 patent. It has been found that runs of ectopy associated with irregular coupling intervals result in a higher density of ($\delta RR_i$, $\delta RR_{i-1}$) data points in segment 9 502 and segment 11 504 as compared to segment 10 506 and segment 12 508. Likewise, during runs of ectopy, a higher density of points tends to occur in segments 5 and 8 (510 and 512) as compared to segments 6 and 7 (514 and 516).

Based on this signature pattern of ($\delta RR_i$, $\delta RR_{i-1}$) data points during runs of frequent ectopic beats, an ectopy cluster signature metric can be computed based on the point counts and number of occupied histogram bins in the above-mentioned segments.

Figure 9:
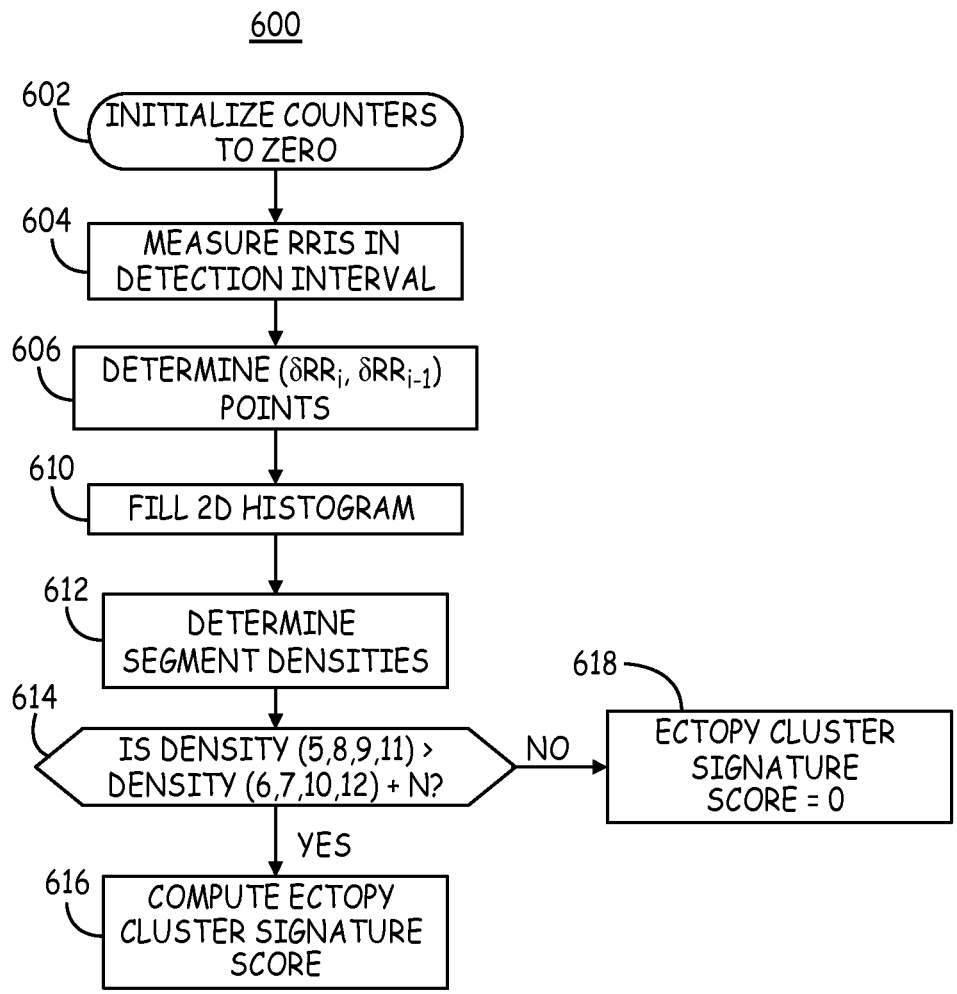
FIG. 9 is a flow chart of a method for analyzing cluster signatures for detecting ectopy in a cardiac rhythm detection algorithm according to one embodiment.

FIG. 9 is a flow chart 600 of a method for analyzing cluster signatures for detecting evidence of ectopy in a cardiac rhythm detection algorithm according to one embodiment. At block 602 histogram counters are initialized to zero. At block 604, RRIs during a detection time interval are measured and used to determine ($\delta RR_i$, $\delta RR_{i-1}$) data points at block 606. The data points are used to populate the 2D histogram representing the Lorenz plot area at block 610. At block 612, the densities of selected segments of the Lorenz plot are determined. The selected segments are chosen based on cluster signature patterns during runs of ectopy, for example as described above in conjunction with FIG. 8.

In one embodiment a segment density is computed using a point count and a bin count for each of the selected segments. A point count is the total number of ($\delta RR_i$, $\delta RR_{i-1}$) data points counted in a given segment of the Lorenz plot. A bin count is a count of the number of populated histogram bins in the segment, i.e. the number of bins having a count greater than zero. A segment density is computed as the difference between the point count and the bin count for the given segment. The segment density is thus a measure of how tightly clustered data points are in a given segment. In other words, segment density is a measure of how many data points there are in a given segment and how many occupied bins those points occupy. Other measures of segment density could be computed. For example a ratio of the point count to the bin count could be determined rather than a difference.

Based on the cluster signature described above in conjunction with FIG. 8, segment densities are determined for segments 5, 8, 9 and 11 (which are preferentially filled during runs of ectopy) and segments 6, 7, 10, and 12 (which are less densely populated during runs of ectopy compared to segments 5, 8, 9 and 11). The densities of segments 5, 8, 9 and 11 are summed to obtain a combined density metric, $Density_{5,8,9,11}$, of those segments. A high combined density of those segments provides positive evidence for ectopy associated with irregular coupling intervals. Likewise, densities of segments 6, 7, 10 and 12 are summed to obtain a combined density metric, $Density_{6,7,10,12}$, of those segments. A high combined density of those segments provides negative evidence for ectopy.

If $Density_{5,8,9,11}$ is not greater than $Density_{6,7,10,12}$, by at least a predetermined amount N, as determined at decision block 614, the distribution of points in the histogram bins does not correspond to an ectopy cluster signature. The ectopy cluster signature metric is set equal to zero at block 618.

The predetermined amount N used in the comparison at block 614 may be zero in some embodiments or may be any value greater than zero. The value N may depend on the number of RRIs measured during the detection time interval or the duration of the detection time interval. In one embodiment using a detection time interval of two minutes, N is given a value of 15 such that the summed densities of segments 5, 8, 9, and 11 must be at least 15 greater than the summed densities of segments 6, 7, 10 and 12.

If $Density_{5,8,9,11}$ is greater than $Density_{6,7,10,12}$, plus a predetermined value N, the cluster signature does correspond to an ectopy cluster signature and provides positive evidence for ectopy associated with irregular coupling intervals. An ectopy cluster signature score is computed at block 616. In one embodiment, the ectopy cluster signature score is set equal to one at block 616. In other embodiments, the ectopy cluster signature score is computed using any of the segment densities computed at block 612. For example, the ectopy cluster signature score may be computed as the difference between the two summed densities less the predetermined value N:

Ectopy cluster signature score=$Density_{5,8,9,11}$−$Density_{6,7,10,12}$−N

The ectopy cluster signature score may be used alone to either adjust the AF evidence score (or other RRI variability metric) as described in conjunction with FIG. 5 or to reject the current detection time interval and hold a previous atrial rhythm classification as described in conjunction with FIG. 6. In still other embodiments, the ectopy cluster signature score may be used to classify the rhythm as a sinus rhythm with frequent ectopy at the end of the detection time interval. For the purpose of providing a rhythm classification output, the ectopy cluster signature score and/or segment densities computed at block 612 may be used alone or in any combination with other ectopy metrics or scores described herein, including the ectopy count metric, RRI mode metric, or RRI ectopy evidence score described in conjunction with FIG. 7, for computing an overall ectopy evidence score.

Figure 10:
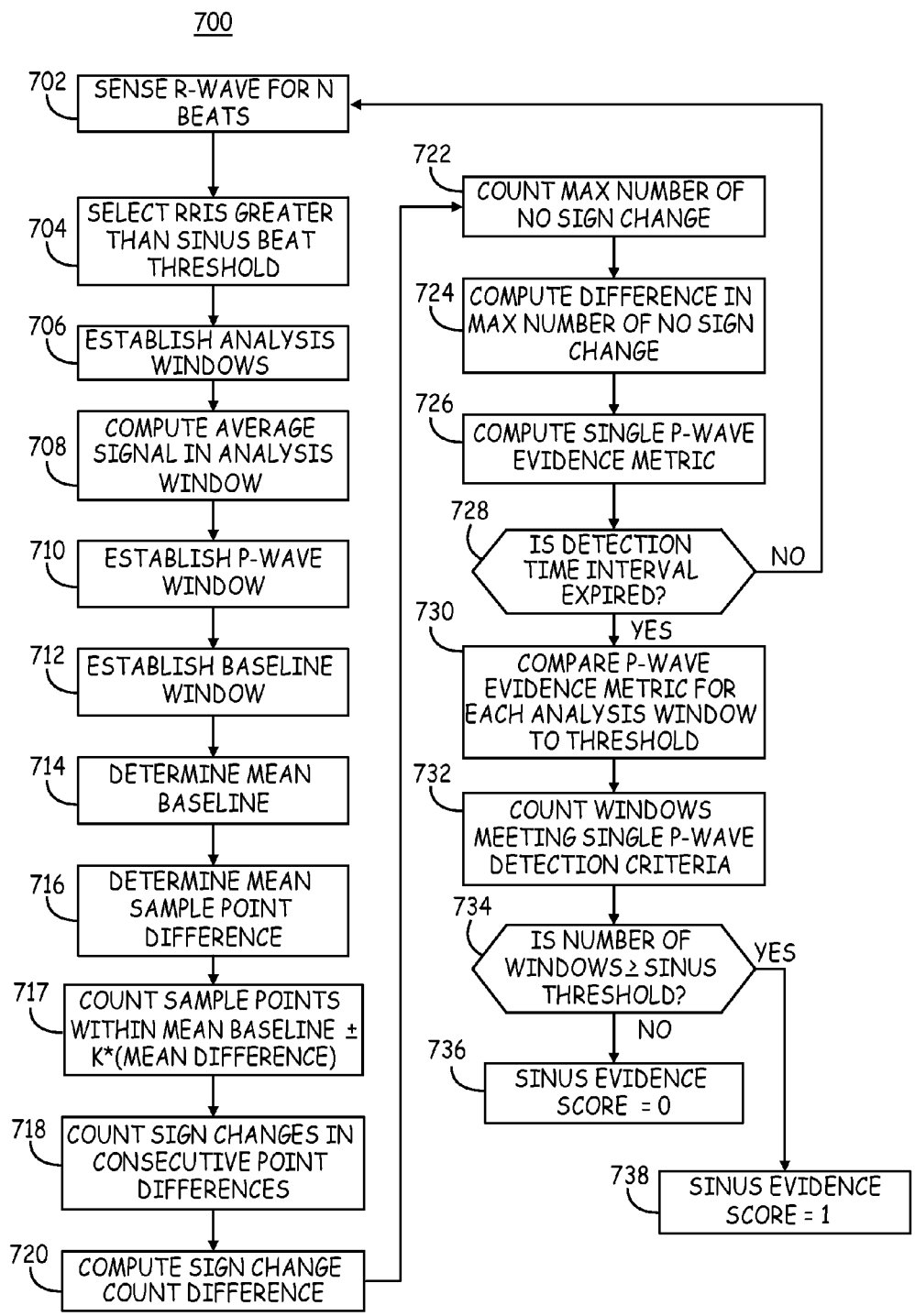
FIG. 10 is a flow chart of a method for detecting evidence of ectopy based on signal morphology during a cardiac rhythm detection algorithm.

FIG. 10 is a flow chart 700 of a method for detecting evidence of ectopy based on signal morphology analysis during a cardiac rhythm detection algorithm. Ectopy may occur in the ventricles, in the atria or both. As such, morphology analysis for detecting evidence of ectopy may include an analysis for detecting PVCs and/or PACs. Morphology analysis may include an analysis of sensed R-waves to detect a morphology corresponding to PVCs. Additionally or alternatively, a morphology analysis of the ventricular signal between sensed R-waves, i.e. during an RRI, may be performed to determine if evidence of a single P-wave within an RRI occurs. The occurrence of a single P-wave in the presence of highly irregular RRIs would be evidence of a run of PACs that are being conducted to the ventricles and are occurring at irregular coupling intervals due to an underlying variable sinus rhythm. Thus, evidence of a single P-wave during an RRI when RRIs are highly variable is treated as positive evidence for a run of ectopy, or another rhythm such as sick sinus rhythm, as opposed to AF.

At block 702, R-waves are sensed from a ventricular EGM or ECG signal. At block 704, RRIs that are greater than a sinus rate threshold are selected. In one embodiment, only RRIs that are at least 700 ms long are selected. Shorter RRIs (i.e. faster heart rates) are generally not selected to promote selection of a baseline morphology analysis window occurring later than the T-wave following the preceding R-wave so that the T-wave does not interfere with a baseline morphology analysis. Evidence for sinus rhythm can be searched for during a long RRI.

Using only the RRIs meeting the sinus rate threshold, a morphology analysis window is established during each RRI at block 706. The established analysis windows for a predetermined number of RRIs are averaged at block 708 to obtain an averaged signal during the analysis window. For example, the EGM/ECG signal during the analysis window of 4, 8, 16, or other number of RRIs that are greater than the sinus beat threshold is averaged at block 708. The RRIs that are averaged may be consecutive RRIs. In some embodiments, no signal averaging is performed and the morphology analysis is performed on each analysis window for individual RRIs. Other filtering of a single RRI analysis window may be performed to remove high frequency noise during the analysis window.

At block 710, a P-wave window during the averaged analysis window is established. At block 712, a baseline window is established during the analysis window. An illustration of these windows is shown in FIG. 11.

Figure 11:
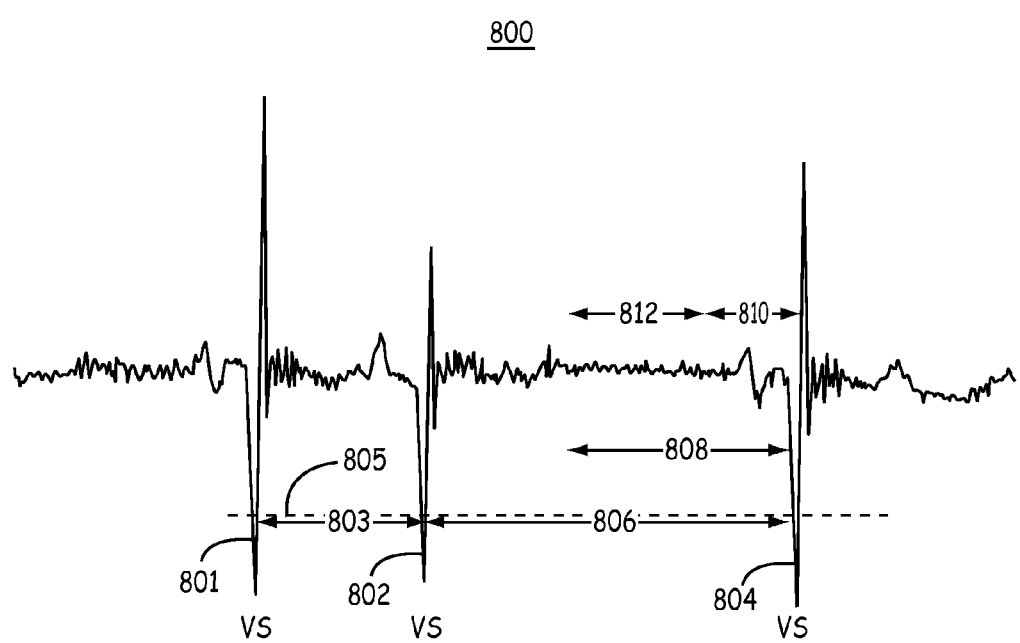
FIG. 11 shows an EGM signal including three sensed R-waves and morphology analysis windows.

In FIG. 11, an EGM signal 800 is shown including three sensed R-waves 801, 802 and 804 each labeled VS. The R-waves 801, 802, 804 are sensed when the EGM signal 800 crosses an R-wave sensing threshold 805. Sensing threshold 805 is shown as a fixed threshold in FIG. 11, but it is recognized than an auto-adjusting threshold may be used.

The first RRI 803 measured between the time R-wave 801 crosses sensing threshold 805 and the time R-wave 802 crosses sensing threshold 805 is too short to meet the sinus rhythm threshold at block 704 of FIG. 10. As such, the RRI 803 is not used in the morphology analysis for ectopy detection. The next RRI 806, measured between sensed R-wave 802 and sensed R-wave 804 is greater than the sinus rhythm threshold and the signal during RRI 806 will be used for ectopy detection. In one embodiment, the sinus threshold is set to be approximately 700 ms.

A morphology analysis window 808 is established as a time interval preceding sensed R-wave 804. In one embodiment, the morphology analysis window is set to be approximately 700 ms, equal to the sinus rhythm threshold used to select RRIs for morphology analysis. The EGM signal during the analysis window 808 may be averaged with other analysis windows selected during other RRIs or may be filtered to remove high frequency noise as described above.

Once an averaged or filtered (or raw) morphology analysis window 808 is established, it is divided into a P-wave window 810 and a baseline window 812. The signal morphology during the P-wave window 810 and during the baseline window 812 is analyzed to detect evidence of a single P-wave occurring during the RRI 806. The P-wave window 810 and the baseline window 812 may be equal or different in length and various metrics determined during windows 810 and 812 may be normalized by the window lengths to allow comparisons of such metrics as needed.

Referring again to FIG. 10, at block 714 a mean baseline amplitude is determined for the baseline window. The mean baseline amplitude is a mean or median value of the signal sample points during the baseline window 812. At block 716, a mean sample point difference is determined for the baseline window 812. The mean sample point difference is the mean or median value of the absolute differences between consecutive EGM signal sample points during the baseline window 812.

The number of sample points within a defined range of the mean baseline amplitude during the baseline window 812 is counted at block 717. A large number of points near the mean or median baseline amplitude indicates a stable baseline without a P-wave during the baseline window 812. The range around the baseline mean is defined as proportion of the mean consecutive sample point difference determined at block 716 in one embodiment. The mean or median absolute difference between consecutive sample points may be multiplied by a factor K, as shown in block 717. The number of sample points falling within a range defined as ±K*mean absolute difference of the mean baseline value is stored as a BASELINE VALUE COUNT at block 717.

Additionally at block 7171, P-WAVE VALUE COUNT may be computed as the number of sample points in the P-wave window falling within the range defined as ±K*mean absolute difference of the mean baseline value. A relatively high BASELINE VALUE COUNT (indicating a stable baseline amplitude) paired with a low P-WAVE VALUE COUNT is evidence of a P-wave during the P-wave window and is thus evidence of a high likelihood of single P-waves occurring during the RRIs.

At block 718, the sign changes between consecutive sample point differences are counted during both the baseline window 812 and the P-wave window 810. Counting the number of sign changes involves first determining the differences in amplitude between consecutive sample points. Next, consecutively determined differences are compared to determine if there is a change in sign or polarity of those differences. For example the difference between point 2 and point 1 may be a positive difference indicating an increasing signal. The difference between point 3 and point 2 may be a negative difference indicating a decreasing signal. This change in sign from a positive difference to a negative difference between the consecutively determined point differences of point 3–point 2 and point 2–point 1 would be counted as a sign change.

A zero difference will be counted as a sign change at block 718. For example if point 2–point 1 is a positive change and point 3 equals point 2 in signal amplitude resulting in a zero sample point difference, the consecutively determined sample point differences of point 3–point 2 and point 2–point 1 will be counted as a sign change. Similarly, if two consecutive sample point differences are both zero, the consecutive sample point differences will be counted as a sign change.

The number of sign changes during the baseline window 812 is stored as a baseline sign change count, and the number of sign changes during the P-wave window 810 is stored as a P-wave sign change count at block 718. At block 720, the difference between the baseline sign change count and the P-wave sign change count is computed and stored as a sign change count difference (SC COUNT DIFF).

A relatively low number of sign changes during the P-wave window is evidence of a P-wave. A far-field P-wave signal is substantially increasing then substantially decreasing on a ventricular EGM or a subcutaneous ECG signal. Frequent or numerous sign changes would not be evidence of the morphology of a P-wave. A relative high number of sign changes, which includes counting sample point differences of zero, during the baseline window is an indication that the presence of a P-wave during the baseline window 812 is unlikely. This evidence of no P-wave during the baseline window 812 paired with infrequent sign changes during the P-wave window 810 indicating the likely presence of a P-wave is strong evidence of a single P-wave during the RRI.

If a high RRI variability metric, such as an AF evidence score, is determined during the rhythm classification algorithm but there is evidence of only a single P-wave during each RRI, this evidence suggests a run of atrial ectopy conducted to the ventricles at irregular coupling intervals. Evidence of more than one P-wave during an RRI would be more likely be associated with AF in which some but not all atrial depolarizations are being conducted to the ventricles.

At block 722, the maximum number of consecutive points corresponding to no sign change in consecutively determined sample point differences is counted for both the baseline window 812 and the P-wave window 810. In counting consecutive points corresponding to no sign change in consecutively determined point-to-point differences, consecutive points of the same value may be counted as a sign change. The difference (NO SC COUNT DIFF) between the maximum number of consecutive points corresponding to no sign change in the baseline window 812 and the maximum number of consecutive points in the P-wave window 810 is computed and stored at block 724. A large difference in the maximum number of consecutive points presenting no sign change supports evidence of a single P-wave. A long run of continuously increasing or decreasing signal sample points during the P-wave window supports evidence of a P-wave while brief or minimal runs of continuously increasing or decreasing signal sample points during the baseline window supports evidence of no additional P-waves during the baseline window.

At block 726, a single P-wave evidence metric is computed using the measurements made during the baseline and P-wave windows. The metric is an indicator of the likelihood that only a single P-wave exists during RRIs. In one embodiment, a single P-wave evidence metric is computed as a weighted combination of the BASELINE VALUE COUNT and P-WAVE VALUE COUNT (determined at block 717), the difference in sign change count between the baseline and P-wave windows (SC COUNT DIFF, determined at block 720) and the difference between the maximum number of points with no sign change in the baseline window and in the P-wave window (MAX NO SC COUNT DIFF, determined at block 724).

If the detection time interval is expired at block 728, the P-wave evidence metric computed at block 726 for each analysis window during the detection time interval is compared to a threshold for detecting a high likelihood of single P-waves during RRIs at block 730. In one embodiment, a single P-wave detection criterion is a weighted sum of the above mentioned metrics (BASELINE VALUE COUNT, P-WAVE VALUE COUNT, SC COUNT DIFF, and MAX NO SC COUNT DIFF) meeting a threshold defined for detecting a high likelihood of single P-waves during RRIs.

In an alternative embodiment, instead of combining the above-mentioned metrics in a weighted combination, each individual parameter may be compared to respective thresholds. The individual threshold comparisons may be combined in a logic operation for detecting whether criteria for detecting a single P-wave are met. For example, logic operations may combine threshold criterion applied to each individual parameter using AND or OR operators and may include applying more than one threshold to each metric. For example if the MAX NO SC COUNT DIFF metric reaches a first high level threshold and BASELINE VALUE COUNT meets a defined threshold, the single P-wave detection criteria may be met independent of SC COUNT DIFF or as long as the SC COUNT DIFF meets at least some low level threshold. If the MAX NO SC COUNT DIFF metric reaches at least a second, lower level threshold one or both BASELINE VALUE COUNT and SC COUNT DIFF may be required to meet relatively more stringent (higher) thresholds for detecting a high likelihood of a single P-wave occurring during each RRI.

In general, X of Y criteria may be satisfied where Y criteria includes multiple thresholds applied to each metric. For example, if three threshold levels are defined for each of four metrics, there exists twelve criteria. If one metric meets its highest threshold, three of the twelve criteria are met. A requirement of, for example, 6 out of 12 (X out of Y) criteria may be applied for detecting an analysis window that supports detection of single P-waves during RRIs.

The number of analysis windows, during the entire detection time interval, meeting criteria for detecting a single P-wave during each RRI is counted at block 732. The count of analysis windows meeting single P-wave detection criteria is compared to a sinus detection threshold at block 734. If the count does not reach the sinus detection threshold for the detection time interval, the sinus evidence score is set equal to zero at block 736. If the count reaches the threshold as determined at block 734, a sinus evidence score is set equal to one at block 738. Alternatively, the evidence score may be computed at block 738 using any combination of the metrics determined in the process shown in FIG. 10, e.g., BASELINE VALUE COUNT, P-WAVE VALUE COUNT, SC COUNT DIFF, MAX NO SC COUNT DIFF, and the count of the number of windows meeting criteria for detecting a single P-wave as determined at block 732.

The sinus evidence score may be used to adjust an AF evidence score (or another metric of RRI variability used to detect and classify a cardiac rhythm), reject the current detection time interval for classifying the cardiac rhythm, or classify the rhythm as a sinus rhythm with ectopy at the expiration of the detection time interval. The sinus evidence score may be combined with other scores or metrics described herein to obtain an overall ectopy evidence score. For example, the sinus score may be combined with the RRI ectopy evidence score described in conjunction with FIG. 7 and/or the ectopy cluster signature score described in conjunction with FIG. 9.

Figure 12:
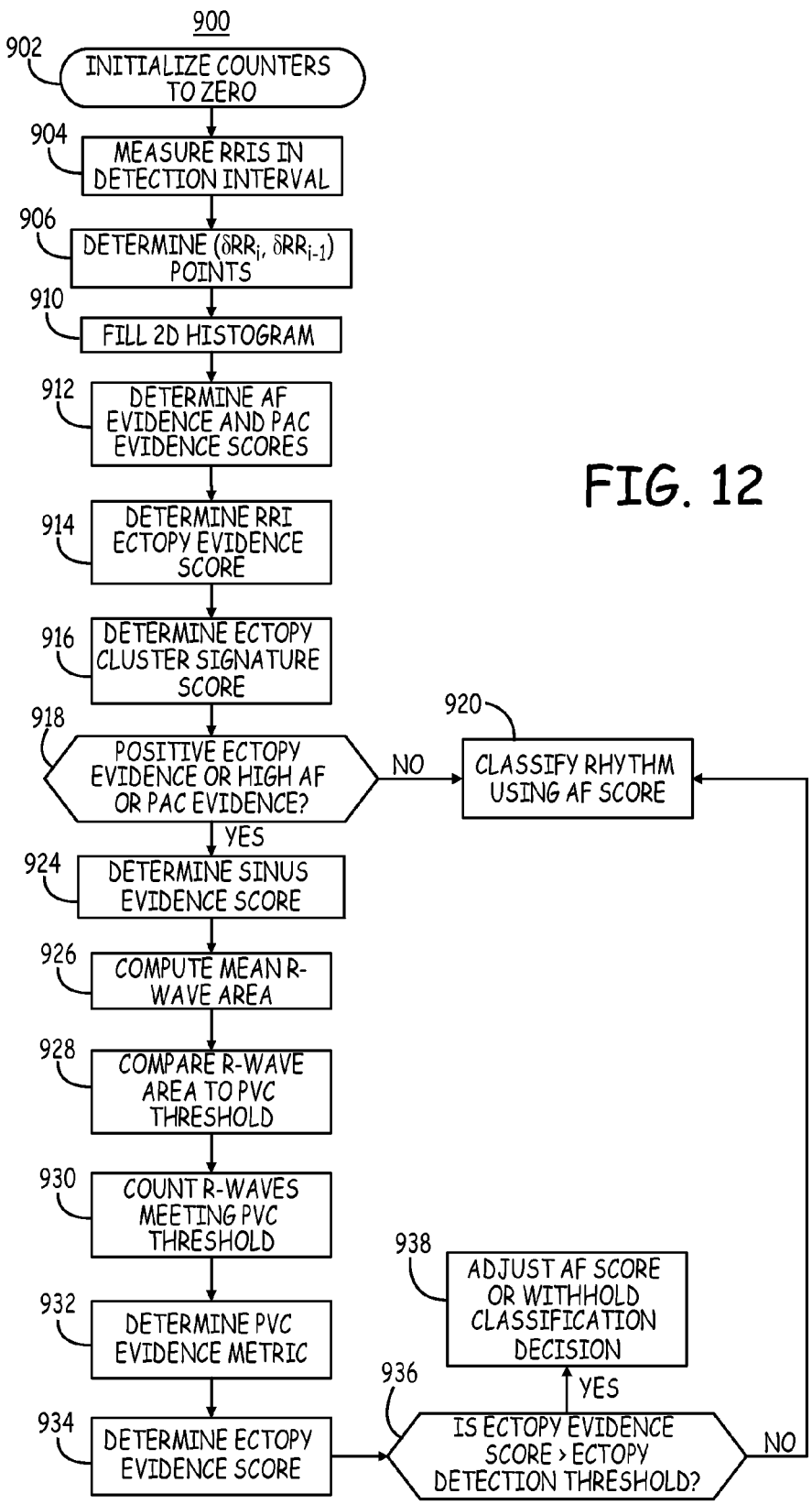
FIG. 12 is a flow chart of a method for determining evidence of ectopy and using that evidence during a cardiac rhythm detection algorithm.

FIG. 12 is a flow chart 900 of a method for determining evidence of ectopy and using that evidence during a cardiac rhythm detection algorithm. At block 902, all counters are initialized to zero values at the beginning of a detection time interval. At block 904, all RRIs are measured during the detection time interval and used to determine ($\delta RR_i$, $\delta RR_{i-1}$) data points at block 906. The ($\delta RR_i$, $\delta RR_{i-1}$) data points are used to populate a Lorenz plot histogram at block 910 as described previously.

At block 912, an AF evidence score and/or other RRI variability score is computed using the distribution of occupied histogram bins and histogram bin counts, e.g. as generally described in any of the above-incorporated '911, '569, '765 and '368 patents. In addition, a regular PAC evidence score may be computed as generally described in the above-incorporated '911 patent. The regular PAC evidence score is computed as a summation of the segment densities in segments 1 through 6 and 10 less a summation of the segment densities in segments 7, 8 and 12 (see FIG. 8 for segment designations). This regular PAC evidence score differs from the ectopy metrics and scores described herein in that the regular PAC evidence score is a measure of a cluster signature particularly associated with PACs that occur at regular coupling intervals and present regular patterns of RRIs, e.g. associated with bigeminy (short-short-long RRIs) or trigeminy (short-short-short-long RRIs). In contrast, the various metrics and scores for detecting evidence of ectopy described herein are directed toward detecting runs of frequent ectopy associated with irregular coupling intervals, resulting in high RRI variability tending toward or resulting in a false AF detection.

At block 914, an RRI ectopy evidence score is determined as described in conjunction with FIG. 7. An ectopy cluster signature score is computed at block 916, as described in conjunction with FIG. 9. At block 918, a decision is made whether to perform morphological analysis of the EGM/ECG signal for detecting morphological evidence of ectopy. Morphological analyses typically require greater processing burden than other ectopy metrics based on RRI measurements or histogram bin counts. Accordingly, in some embodiments, morphology analysis is performed only when triggered by other RRI-based metrics or scores that indicate a need for further analysis to detect the possible presence of ectopy, e.g. to reduce the likelihood of runs of ectopy being falsely detected as AF.

In one embodiment, if one or both of the RRI ectopy evidence score and the ectopy cluster signature score provide positive evidence for ectopy, the process advances to block 924 to perform signal morphology analysis for detecting evidence of ectopy. Positive evidence for ectopy could be a score set equal to one or a computed score based on a combination of determined metrics exceeding an ectopy detection threshold.

Additionally or alternatively, if the AF evidence score and/or the regular PAC evidence score reach a threshold level, the morphology analysis may be triggered. For example, if another score determined based on histogram bin counts, such as the AF evidence score or the regular PAC evidence score are demonstrating an increasing trend over consecutive detection time intervals or are near a detection threshold, the morphology analysis may be triggered. The morphology analysis may not be performed unless there is high evidence of both ectopy based on the RRI ectopy evidence score, the ectopy cluster signature score, and the regular PAC evidence score as well as high evidence of RRI variability based on an AF evidence score, or any combination thereof. In this way, the higher processing burden of the morphology analysis is not imposed unless needed to confirm other ectopy evidence and reduce the likelihood of a false AF detection when AF detection criteria are met or close to being met. Thus one or more of these scores relating to positive evidence of ectopy or positive evidence of RRI irregularity may be compared to respective thresholds at block 918 for determining whether morphology analysis for ectopy detection is warranted.

If criteria for triggering a morphology analysis are not met at block 918, the cardiac rhythm is classified at the end of the detection time interval at block 920. The classification is based on cluster signature metrics, such as an AF evidence score, or other measures of the distribution and counts of occupied histogram bins. Ectopy is not determined to be present or at least not considered to be frequent enough to be a confounding factor in making an atrial rhythm classification at the end of the detection time interval using the histogram bin counts and RRI variability scores determined there from.

If morphology analysis is triggered in response to the determination at block 918, a sinus evidence score is determined at block 924 as described in conjunction with FIG. 10. The sinus evidence score provides evidence of a run of PACs conducted to the ventricles at irregular coupling intervals, e.g. due to an underlying variability in sinus rhythm.

Additionally or alternatively, morphology analysis may be performed to detect evidence of PVCs. It is recognized that numerous morphology based methods for detecting PVCs may be employed, including wavelet or other morphology template feature comparisons. In one embodiment, a mean or median R-wave area is determined for the detection time interval at block 926. A mean or median R-wave area may be computed by first determining an R-wave width and an R-wave amplitude.

The width may be determined as the amount of time that a sensed R-wave signal exceeds a defined threshold during an R-wave window set around the sensed R-wave. The amplitude may be determined as the maximum signal sample point during the R-wave window, or more specifically during the R-wave width. The area of the R-wave can then be computed as the product of the width and area. The R-wave area is computed for each sensed R-wave during the detection time interval. A mean or median R-wave area is then determined for the accumulated individual R-wave areas at the expiration of the detection time interval.

Each individual R-wave area is compared to a PVC detection threshold at block 928. The PVC detection threshold may be defined based on the mean or median R-wave area computed at block 926. For example, the PVC detection threshold may be a percentage greater than the mean or median R-wave area.

The R-wave areas meeting or exceeding the PVC detection threshold are counted at block 930. At block 932, a PVC evidence metric may be set equal to the number of R-waves detected as PVCs based on the count determined at block 930. Alternatively a PVC evidence metric may be set equal to one at block 932 if the count reaches a threshold for detecting a run of PVCs and set equal to zero if the count does not reach the threshold. The count at block 930 or the PVC evidence metric set at block 932 may be combined with the number of RRI windows meeting criteria for detecting a single P-wave (block 732 of FIG. 10) to compute or set a frequent ectopy metric.

The various metrics and scores determined as described in conjunction with FIGS. 7, 9, 10 and in the foregoing description of FIG. 12 may be used, in any combination, to determine an overall ectopy evidence score at block 934. A weighted sum, combination of logic operations, or other methods may be used to determine the overall ectopy evidence score. Alternatively, the various metrics and scores for detecting ectopy may be combined in a series of logic operations to detect evidence of a run of ectopy during the detection time interval.

If evidence of a run of ectopy is detected at decision block 936 based on a threshold comparison or logic operations, this evidence is used to adjust the AF score (or other RRI variability metric) at block 938. Alternatively, The ectopy evidence score determined at block 934 may be used directly to adjust the AF score at block 938 without a threshold comparison at block 936.

In other embodiments, positive evidence for a run of ectopy during the detection time interval is used at block 938 to withhold a rhythm classification decision at the expiration of the detection time interval. If the overall ectopy evidence score or logic operation using the various ectopy metrics and scores described herein, alone or in any combination, do not result in positive evidence for frequent ectopy, the rhythm is classified at the expiration of the detection time interval at block 920 using the AF evidence score and/or any other RRI variability metric determined from the populated Lorenz plot histogram bins.

Thus, an apparatus and method have been presented in the foregoing description with reference to specific embodiments for detecting evidence of ectopy and using that evidence in a cardiac rhythm detection and classification algorithm. It is appreciated that various modifications to the referenced embodiments may be made without departing from the scope of the disclosure as set forth in the following claims.

The invention claimed is:

1. A method for classifying a cardiac rhythm, comprising:
obtaining a signal comprising cardiac cycle length information in a patient;
determining cycle lengths in a first heart chamber from the signal during an established time interval;
determining differences between consecutive ones of the cycle lengths in the first heart chamber;
detecting evidence of ectopy associated with irregular coupling intervals from the signal during the established time interval, wherein detecting the evidence of ectopy comprises incrementing a counter in response to a difference between the consecutive ones of the cycle lengths in the first heart chamber being associated with an ectopic event, and comparing the counter to an ectopy count threshold at the expiration of the time interval, and detecting the evidence of ectopy as a likely run of frequent ectopic events during the established time interval if the counter exceeds the ectopy count threshold; and providing a rhythm classification output corresponding to a second heart chamber at the expiration of the established time interval in response to the consecutive cycle length differences and the evidence of ectopy associated with irregular coupling intervals, wherein detecting the evidence of ectopy reduces the likelihood of the rhythm classification being fibrillation in the second heart chamber, wherein the first heart chamber is a ventricular chamber and the second heart chamber is an atrial chamber.

2. The method of claim 1, wherein detecting evidence of ectopy associated with irregular coupling intervals comprises computing an ectopy evidence score in response to the determined cycle lengths.

3. The method of claim 2, wherein detecting evidence of ectopy comprises:
  detecting an ectopic beat sequence from a series of consecutive cycle lengths comprising at least one cycle length corresponding to an ectopic coupling interval and a cycle length immediately following the ectopic coupling interval that is greater than a cycle length immediately preceding the ectopic coupling interval;
  counting the number of ectopic beat sequences detected during the established time interval; and
  comparing the number to an ectopy detection threshold.

4. The method of claim 2, wherein detecting evidence of ectopy comprises:
  determining a mode of the cardiac cycle lengths during the established time interval;
  comparing the mode to a threshold; and
  detecting an underlying sinus rhythm associated with the ectopy occurring at irregular coupling intervals in response to the mode meeting the threshold.

5. The method of claim 1, wherein detecting evidence of ectopy associated with irregular coupling intervals comprises:
  generating a plot corresponding to the determined differences;
  counting a number of the differences in a plurality of segments of the plot defined by a range of magnitudes and phases relative to an origin of the plot;
  determining a first number of differences in a first segment of the plurality of segments, the first segment corresponding to a pattern of the determined differences associated with ectopy occurring at irregular coupling intervals;
  determining a second number of differences in a second segment of the plurality of segments, the second segment corresponding to a pattern of the determined differences not associated with ectopy occurring at irregular coupling intervals; and
  generating an ectopy evidence output in response to the first number of differences and the second number of differences.

6. The method of claim 5 further comprising determining a first density of the differences in the first segment and a second density of the differences in the second segment, wherein the ectopy evidence output is generated using the first density and the second density.

7. The method of claim 1, wherein detecting evidence of ectopy comprises:
  detecting a variability of the determined cycle lengths in response to the determined differences;
  determining a morphology metric from the signal during a cycle length in response to detecting the cycle length variability; and
  generating an ectopy evidence output in response to the morphology metric.

8. The method of claim 7, further comprising:
  establishing a morphology analysis window within the cardiac cycle length;
  establishing a baseline portion and a signal portion of the analysis window;
  determining a number of sign changes between consecutive signal point differences during each of the baseline portion and the signal portion; and
  generating the ectopy evidence output in response to the number of sign changes during the baseline portion and during the signal portion.

9. The method of claim 8, further comprising:
  generating the ectopy evidence output for a plurality of analysis windows established during the established time interval; and
  detecting ectopy associated with irregular coupling intervals in response to the ectopy evidence output generated for the plurality of analysis windows.

10. The method of claim 7, wherein detecting the ectopy evidence comprises determining an ectopy evidence output corresponding to a single cardiac event occurring in the second chamber in response to the morphological metric determined from the signal during the determined cycle length in the first chamber.

11. The method of claim 1, wherein providing the rhythm classification output comprises one of providing a value for adjusting a metric of variability determined from the differences and used for classifying the second heart chamber rhythm and a providing a rejection of the established time interval for use in classifying the second heart chamber rhythm.

12. A medical device for classifying a cardiac rhythm, comprising:
  a sensor to sense a signal comprising cardiac cycle length information in a patient; and
  a processor to receive the signal and configured to:
  determine cycle lengths in a first heart chamber from the signal during an established time interval;
  determine differences between consecutive ones of the cycle lengths in the first heart chamber;
  detect evidence of ectopy associated with irregular coupling intervals from the signal during the established time interval, wherein detecting the evidence of ectopy comprises incrementing a counter in response to a difference between the consecutive ones of the cycle lengths in the first heart chamber being associated with an ectopic event, comparing the counter to an ectopy count threshold at the expiration of the time interval, and detecting the evidence of ectopy as a likely run of frequent ectopic events during the established time interval if the counter exceeds the ectopy count threshold; and
  generate a rhythm classification output corresponding to a second heart chamber at the expiration of the established time interval in response to the consecutive cycle length differences and the evidence of ectopy associated with irregular coupling intervals, wherein detecting the evidence of ectopy reduces the likelihood of the rhythm classification being fibrillation in the second heart chamber, wherein the first heart chamber is a ventricular chamber and the second heart chamber is an atrial chamber.

13. The device of claim 12, wherein detecting evidence of ectopy associated with irregular coupling intervals comprises computing an ectopy evidence score in response to the determined cycle lengths.

14. The device of claim 13, wherein detecting evidence of ectopy comprises:
detecting an ectopic beat sequence from a series of consecutive cycle lengths comprising at least one cycle length corresponding to an ectopic coupling interval and a cycle length immediately following the ectopic coupling interval that is greater than a cycle length immediately preceding the ectopic coupling interval;
counting the number of ectopic beat sequences detected during the established time interval; and
comparing the number to an ectopy detection threshold.

15. The device of claim 13, wherein detecting evidence of ectopy further comprises:
determining a statistical mode of the cardiac cycle lengths during the established time interval;
comparing the mode to a threshold; and
detecting an underlying sinus rhythm associated with the ectopy occurring at irregular coupling intervals in response to the mode meeting the threshold.

16. The device of claim 12, wherein detecting evidence of ectopy associated with irregular coupling intervals comprises:
generating a plot corresponding to the determined differences;
counting a number of the differences in a plurality of segments of the plot defined by a range of magnitudes and phases relative to an origin of the plot;
determining a first number of differences in a first segment of the plurality of segments, the first segment corresponding to a pattern of the determined differences associated with ectopy occurring at irregular coupling intervals;
determining a second number of differences in a second segment of the plurality of segments, the second segment corresponding to a pattern of the determined differences not associated with ectopy occurring at irregular coupling intervals; and
generating an ectopy evidence output in response to the first number of differences and the second number of differences.

17. The device of claim 16, further comprising determining a first density of the differences in the first segment and a second density of the differences in the second segment, wherein the ectopy evidence output is generated using the first density and the second density.

18. The device of claim 12, wherein detecting evidence of ectopy comprises:
detecting a variability of the determined cycle lengths in response to the determined differences;
determining a morphology metric from the signal during a cycle length in response to detecting the cycle length variability; and
generating an ectopy evidence output in response to the morphology metric.

19. The device of claim 18, further comprising:
establishing a morphology analysis window within the cardiac cycle length;
establishing a baseline portion and a signal portion of the analysis window;
determining a number of sign changes between consecutive signal point differences during each of the baseline portion and the signal portion; and
generating the ectopy evidence output in response to the number of sign changes during the baseline portion and during the signal portion.

20. The device of claim 19, further comprising:
generating the ectopy evidence output for a plurality of analysis windows established during the established time interval; and
detecting evidence of ectopy associated with irregular coupling intervals in response to the ectopy evidence output generated for the plurality of analysis windows.

21. The device of claim 18, wherein detecting the ectopy evidence comprises determining an ectopy evidence output corresponding to a single cardiac event occurring in the second chamber in response to the morphological metric determined from the signal during the determined cycle length in the first chamber.

22. The device of claim 12, wherein generating the rhythm classification output comprises one of providing a rejection of the established time interval for use in classifying the second heart chamber rhythm and providing a value for adjusting a metric of variability determined from the differences and used for classifying the second heart chamber rhythm.

23. A non-transitory computer-readable medium storing a set of instructions which cause a processor of an implantable medical device to perform a method comprising:
obtaining a signal comprising cardiac cycle length information in a patient;
determining cycle lengths in a first heart chamber from the signal during an established time interval;
determining differences between consecutive ones of the cycle lengths in the first heart chamber;
detecting evidence of ectopy associated with irregular coupling intervals from the signal during the established time interval, wherein detecting the evidence of ectopy comprises incrementing a counter in response to a difference between the consecutive ones of the cycle lengths in the first heart chamber being associated with an ectopic event, comparing the counter to an ectopy count threshold at the expiration of the time interval, and detecting the evidence of ectopy as a likely run of frequent ectopic events during the established time interval if the counter exceeds the ectopy count threshold; and
providing a rhythm classification output corresponding to a second heart chamber at the expiration of the established time interval in response to the consecutive cycle length differences and the evidence of ectopy associated with irregular coupling intervals wherein detecting the evidence of ectopy reduces the likelihood of the rhythm classification being fibrillation in the second heart chamber, wherein the first heart chamber is a ventricular chamber and the second heart chamber is an atrial chamber.

24. A medical device for classifying a cardiac rhythm, comprising:
a sensor to sense a signal comprising cardiac cycle length information in a patient; and
a processor to receive the signal and configured to:
determine cycle lengths in a first heart chamber from the signal during an established time interval;
determine differences between consecutive ones of the cycle lengths in the first heart chamber;
from the determined differences, determine a count of sequences of the consecutive ones of the cycle lengths comprising a first cycle length, a second cycle length consecutively following the first cycle length and shorter than the first cycle length and a third cycle length consecutively following the second cycle length and longer than the first cycle length;

compare the count to an ectopy count threshold for positively identifying a run of frequent ectopic events during the established time interval;

generate a rhythm classification output corresponding to a second heart chamber at the expiration of the established time interval in response to the consecutive cycle length differences and the count, wherein the count being greater than the threshold reduces the likelihood of the rhythm classification being fibrillation in the second heart chamber.

* * * * *